United States Patent [19]
Parten et al.

[11] Patent Number: 5,980,696
[45] Date of Patent: Nov. 9, 1999

[54] DEHYDRATION OF ACETIC ACID BY AZEOTROPIC DISTILLATION IN THE PRODUCTION OF AN AROMATIC ACID

[75] Inventors: William David Parten, Near Stokesley; Alan Macpherson Ure, Stocton-on-Tees, both of United Kingdom

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,979

[22] PCT Filed: Aug. 16, 1995

[86] PCT No.: PCT/GB95/01933

§ 371 Date: Feb. 5, 1997

§ 102(e) Date: Feb. 5, 1997

[87] PCT Pub. No.: WO96/06065

PCT Pub. Date: Feb. 29, 1996

[30] Foreign Application Priority Data

Aug. 23, 1994 [GB] United Kingdom .................... 9416978
Aug. 23, 1994 [GB] United Kingdom .................... 9416980

[51] Int. Cl.[6] .............................. B01D 3/36; B01D 3/42; C07C 51/46
[52] U.S. Cl. .................. 203/1; 159/DIG. 19; 203/15; 203/16; 203/60; 203/96; 203/97; 203/98; 203/99; 203/DIG. 19; 562/608; 202/158
[58] Field of Search .................. 203/60, 16, 2, 203/1, DIG. 18, 15, 14, 92–94, 95–98, 99, DIG. 19, DIG. 6, DIG. 21, 86; 562/608, 409, 414, 485; 159/DIG. 19; 560/248; 202/158

[56] References Cited

U.S. PATENT DOCUMENTS

| | | | |
|---|---|---|---|
| 1,860,512 | 5/1932 | Ricard et al. | 203/60 |
| 1,917,391 | 7/1933 | Othmer . | |
| 2,050,234 | 8/1936 | Othmer . | |
| 2,050,235 | 8/1936 | Othmer | 203/60 |
| 2,317,758 | 4/1943 | Guinot | 203/60 |
| 2,395,010 | 2/1946 | Othmer . | |
| 2,667,502 | 1/1954 | Steitz, Jr. et al. | 203/60 |
| 2,801,265 | 7/1957 | Coutor | 203/60 |
| 3,052,610 | 9/1962 | Araboshi et al. | 203/60 |
| 3,394,058 | 7/1968 | Hohenschutz | 203/60 |
| 3,844,903 | 10/1974 | Willersinn et al. | 203/60 |
| 4,204,915 | 5/1980 | Kurata et al. | 203/60 |
| 4,250,330 | 2/1981 | Constantini et al. . | |
| 4,314,947 | 2/1982 | Hohenschutz et al. | 202/158 |
| 5,409,579 | 4/1995 | Gualy et al. | 203/16 |

FOREIGN PATENT DOCUMENTS

| | | | |
|---|---|---|---|
| 9105989 | 8/1991 | Rep. of Korea . | |
| 298137 | 9/1929 | United Kingdom . | |
| 273 744 | 12/1929 | United Kingdom . | |
| 0788931 | 1/1958 | United Kingdom | 203/60 |
| 1039934 | 8/1966 | United Kingdom . | |
| 1576787 | 10/1980 | United Kingdom . | |
| 1593117 | 7/1981 | United Kingdom . | |

OTHER PUBLICATIONS

Othmer, D.F., Azeotropic Separation, Chemical Engineering Progress, vol. 59, No. 6, pp. 67–78.

*Primary Examiner*—Virginia Manoharan
*Attorney, Agent, or Firm*—Charles E. Krukiel

[57] ABSTRACT

An improved process for preparing an aromatic dicarboxylic acid wherein the improvement resides in dehydrating and recovering solvent from a feed stream having from 20% to 40% by weight water via azeotropic distillation with organic phase reflux using an entrainer selected from isobutyl acetate, n-propyl acetate or an entrainer with a boiling point between isobutyl acetate and n-propyl acetate.

7 Claims, 3 Drawing Sheets

DEHYDRATION OF ACETIC ACID BY AZEOTROPIC DISTILLATION IN THE PRODUCTION OF AN AROMATIC ACID

This invention relates to separation of water from a liquid phase medium containing water and at least one other component.

The invention has particular application to the separation of water from an aqueous feed stream containing an aliphatic carboxylic acid such as acetic acid.

A specific application of the invention is in a process for the production of an aromatic dicarboxylic acid such as terephthalic acid in which, to remove water generated in the reaction producing the dicarboxylic acid, an acetic acid/water vapor stream is drawn off from the reactor overheads and subjected to distillation to separate the water from the acetic acid. The dehydrated acetic acid is then recycled at least in part to the oxidation reactor. Traditionally fractional distillation has been used for this task since the manufacture of terephthalic acid is a process which, when operated at elevated pressures (typically in excess of 20 bara), produces significant waste heat which is available for use as reboil heat for the distillation column.

However, with the advent of interest in lower pressure processes for the manufacture of terephthalic acid combined with a drive for more efficient heat recovery schemes, heterogeneous azeotropic distillation has been recognised as offering potential capital and variable cost benefits over fractional distillation.

Heterogeneous azeotropic distillation for acetic acid/water separation is disclosed in U.S. Pat. No. 2,050,234, U.S. Pat. No. 4,250,330 and GB-A-1576787. As stated in GB-A-1576787, a significant advantage of azeotropic distillation is low reflux ratio and hence reduced heat energy requirement for distillation. Reflux ratio is dependent on the particular entrainer selected for the azeotropic distillation. In terms of low reflux ratios, n-butyl acetate (boiling point: about 126.2° C.) must be considered. This particular entrainer is favoured in GB-A-1576787 for the separation of acetic acid and water. Less desirable from the standpoint of reflux ratio is the lower boiling point entrainer isobutyl acetate (boiling point: about 117° C.) which is favoured by U.S. Pat. No. 4,250,330; even less desirable in this context is n-propyl acetate (boiling point: about 101° C.) which was found to be useful as an entrainer in the 1930's prior to the recognition of n-butyl acetate as a superior entrainer (see U.S. Pat. No. 2,050,234 which is concerned with the production of substantially pure "glacial" acetic acid from aqueous acetic acid). N-butyl acetate is advantageous because of the higher amount of water entrained in the azeotrope which allows a lower reflux ratio when organic phase reflux only is used.

In the kind of application that the present invention is specifically concerned with, it is not necessary for the distillation to be carried out in such a way as to produce substantially anhydrous acetic acid. Because the acetic acid is to be recycled at least in part to the oxidation reactor, it is expedient to produce a partially dehydrated acetic acid product typically containing of the order of 5% by weight water based on the combined acetic acid/water content. U.S. Pat. No. 4,250,330 and GB-A-1576787 both contemplate the possibility of producing a bottoms product containing some water; U.S. Pat. No. 4,250,330 mentions a water content of no more than 10% (and preferably no more than 5%) by weight using isobutyl acetate entrainer whilst GB-A-1576787 gives a specific Example in which, using n-butyl acetate entrainer, the water content in the dehydrated acetic acid product is 6.3% by weight.

In GB-A-1576787 a bottoms product containing water is obtained using n-butyl acetate entrainer and, apart from using an excessive number of trays in the bottom part of the distillation column, slippage of entrainer into the bottoms product can only be avoided by employing a feed stream which has a high water content and/or by using a reflux combining both organic (entrained and aqueous phases. Thus, in the Example given in GB-A-1576787, the water content of the feed stream supplied via feed line 5 comprises 56.51% by weight of water relative to the acetic acid content of the feed stream. Nowadays terephthalic acid production installations tend to employ relatively low water content in the oxidation reactor (eg about 8% by weight based on the combined liquid phase acetic acid/water content) in order to minimise corrosion and burning of acetic acid and hence loss of solvent. Thus, for plant operating with relatively low water content in the oxidation reactor, if the feed stream to the distillation column is derived from the reactor overheads, to achieve a water content in the feed stream of for example 56% by weight, it would be necessary to use a rectifier or equivalent water concentration device upstream of the azeotropic distillation column, ie to produce from the relatively low water content in the condensed acetic acid/water reactor overheads a water rich feed stream for treatment in the azeotropic distillation column. Moreover, in the Example of GB-A-1576787, it will be noted that the reflux to the distillation column is a combined feed of organic and aqueous phases.

In U.S. Pat. No. 4,250,330, the water content of the feed stream to the distillation column is not specifically disclosed but, according to Example 1, the feed stream is made up of acetic acid/water vapor derived from a partially anhydrifying column supplied with mother liquor (line 1) and a liquid stream of aqueous acetic add at 70% by weight (line 8) derived from other parts of the plant. Significantly, FIG. 1 of the drawings illustrates the provision of a line 17 which will be effective to recycle part of the aqueous phase back to the distillation column so that the reflux comprises a combined feed of organic and aqueous phase components. Apparently the aqueous phase component was considered necessary in order to avoid slippage of entrainer into the bottoms product.

Although the azeotropic distillation systems of U.S. Pat. No. 4,250,330 and GB-A-1576787 can be operated using n-butyl or isobutyl acetate entrainers, from the foregoing it will be seen that certain compromises have to be made in order to secure a water-containing bottoms product which is substantially free of entrainer.

According to one aspect of the present invention there is provided a process for the production of an aromatic dicarboxylic acid comprising oxidising a precursor of the dicarboxylic acid in an aqueous liquid phase medium comprising a lower aliphatic carboxylic acid and in the presence of a heavy metal catalyst system, the oxidation being accompanied by the production of an overhead vapor stream comprising the aliphatic carboxylic add and water, condensing the overhead vapor stream to produce a liquid phase feed stream containing the aliphatic carboxylic acid and water, and azeotropically distilling the feed stream to produce a bottoms product containing the aliphatic carboxylic acid and a reduced amount of water, characterised in that:

(a) the feed stream subjected to azeotropic distillation has a water content within the range 20% to 40% by weight based on the combined weight of the aliphatic carboxylic acid and water in the feed stream;
  (b) isobutyl acetate, n-propyl acetate or an entrainer with a boiling point intermediate those of isobutyl acetate and n-propyl acetate is used as the entrainer;

(c) the distillation is operated with a single organic phase reflux comprising said entrainer; and (d) a bottoms product substantially free of said entrainer is produced which contains an amount of water within the range 2 to 12% by weight based on the combined weight of the aliphatic carboxylic acid and water in the bottoms product.

According to a second aspect of the present invention there is provided a process for the production of an aromatic dicarboxylic acid comprising oxidising a precursor of the dicarboxylic acid in an aqueous liquid phase medium comprising a lower aliphatic carboxylic acid and in the presence of a heavy metal catalyst system, the oxidation being accompanied by the production of an overhead vapor stream comprising the aliphatic carboxylic acid and water, condensing the overhead vapor stream to produce a liquid phase feed stream containing the aliphatic carboxylic acid and water, and azeotropically distilling the feed stream in a distillation column to produce a bottoms product containing the aliphatic carboxylic acid and a reduced amount of water, characterised in that the overhead vapor stream from the reactor is processed with or without the addition of water from other sources to produce a feed stream having a water content of 20 to 40% by weight relative to the combined acetic acid and water in the feed stream and such that the azeotropic distillation can be carried out using as entrainer n-propyl acetate or isobutyl acetate or an entrainer having an intermediate boiling point and using organic phase reflux only while securing a bottoms product which contains between 2 and 12% water by weight based on the combined acetic acid and water content and is substantially entrainer free.

Whilst, in practising the process as defined in the above defined aspects of the invention, it is not contemplated that there will be any reflux of the aqueous phase, we do not exclude the possibility that an insignificant amount (eg no more than 1% and certainly no more than 2% by weight of the total reflux) of the aqueous phase may be refluxed.

Where the water content of the feed stream is below 30% by weight, the presently preferred entrainer is n-propyl acetate.

Preferably the water content of the feed stream comprises 20 to 30% (more preferably 23 to 27%) by weight based on the combined acetic acid and water content of the feed stream.

Usually the water content of the bottoms product comprises 3 to 10% (preferably 3 to 7% and more preferably 4 to 5%) by weight based on the combined acetic acid and water content of the bottoms product.

Where water is added to the feed stream from other sources, the amount added will be a minor proportion of the total water content. Typically the amount added will form no more than 5% (more usually no more than 3%) by weight of the combined acetic acid and water content of the feed stream.

In contrast with U.S. Pat. No. 4,250,330 and GB-A-1576787 the azeotropic distillation process of the present invention is carried out without resorting to a reflux comprising an organic phase and a significant amount of the aqueous phase thereby avoiding complexity in the column overheads system. Also, it is not necessary to take special measures to increase the water content of the feed stream to avoid slippage of entrainer into the bottoms product.

Another advantage secured by the process of the invention is that the column height may be reduced significantly compared with a fractional distillation column or azeotropic distillation column operating with n-butyl acetate as the entrainer. For instance, whilst a conventional fractional distillation column may use 52 theoretical stages and an azeotropic distillation column operating with n-butyl acetate as entrainer may require 40 theoretical stages, a column operating in accordance with the process of the invention may have 35 theoretical stages in the case of isobutyl acetate entrainer and as few as 24 theoretical stages in the case of n-propyl acetate.

An important advantage stemming from the use of a single phase reflux is that a packed column (with a random or structured packing) may be used instead of a trayed column. Where the reflux comprises two phases, the use of a packed column gives rise to distribution problems which would require the use of specially designed redistributors to ensure a uniform liquid phase composition. Thus, in accordance with a preferred aspect of the invention, the azeotropic distillation is carried out in a packed column (provided with a random packing, eg Raschig or Pall rings, or a structured packing). This confers a number of potential advantages over a trayed column, eg column size and column hold-up inventory may be reduced which in turn increases control stability, speeds up response to upsets such as partial or total loss of feed to the column or feed composition changes, and reduces the volume of material dumped into the bottom of the column in the event of loss of reboiler heat.

In the production of aromatic dicarboxylic acids such as terephthalic acid, the reactor overheads vapor stream tends to carry over amounts of the precursor (eg paraxylene) which should desirably be recovered. In a further aspect thereof, the present invention is concerned with the recovery of the precursor in an efficient manner.

According to this aspect of the present invention there is provided a process for the production of an aromatic dicarboxylic acid comprising oxidising a precursor of the dicarboxylic acid in an aqueous liquid phase medium comprising a lower aliphatic carboxylic acid and in the presence of a heavy metal catalyst system, the oxidation being accompanied by the production of an overhead vapor stream comprising the aliphatic carboxylic acid, said precursor and water, condensing the overhead vapor stream to produce a liquid phase feed stream containing the aliphatic carboxylic acid, water and said precursor, and distilling the feed stream in a column to produce a bottoms product containing the aliphatic carboxylic acid and a reduced amount of water, characterised in that said precursor is recovered by:

carrying out the distillation using an entrainer which is capable of forming a heterogeneous azeotrope with water;

controlling penetration of the entrainer whereby the bottoms product is substantially entrainer free;

introducing the feed stream into the column at a location above the lower limit of the azeotropic zone; and withdrawing said precursor from the column in the region of the location of introduction of the feed stream.

In practice, the point at which the feed stream is introduced into the column will be consistent with the need to minimise the concentration of the aliphatic acid in the tops product withdrawn at the upper end of the column and will be somewhat closer to the lower limit of the azeotropic zone than to the top of the column.

This aspect of the invention is based on the surprising finding that the concentration of the precursor is increased substantially in the vicinity of the point of entry of the feed stream. In particular, the ratio between the concentrations of the precursor and the entrainer has been found to peak at a location a short distance below the point of entry of the feed stream.

In one embodiment of the invention, the dicarboxylic acid is terephthalic acid and the precursor is paraxylene.

The entrainer is conveniently one which allows the azeotropic distillation to be carried out using an organic phase reflux only, especially in circumstances where the feed stream to the distillation column contains a water content of no more than 40% (more usually no more than 35%) by weight based on the combined aliphatic acid/water content of the feed stream and where the bottoms product is required to be substantially free of entrainer and have a water content of from 2 to 12% by weight based on the aliphatic acid/water content of the bottoms product.

In this aspect of the invention, the entrainer is preferably constituted by an alkyl acetate, eg iso-butyl acetate or an entrainer having a boiling point lower than iso-butyl acetate (eg n-propyl acetate).

As used throughout this specification, "azeotropic zone" refers to that region of the distillation column where the concentration of the entrainer in the combnd liquid phases is at least 0.1% by weight.

Another aspect of the invention relates to control of an azeotropic distillation column so as to cope with changes in the composition of the feed(s) to the column and/or substantial or total loss of feed.

According to this aspect of the present invention there is provided a process for effecting the separation of water from a liquid phase medium containing at least one other component by azeotropic distillation wherein the tops component primarily comprises water whilst the bottoms product comprises said component and a reduced amount of water, characterised in that the amount of water in the bottoms product is controlled by regulation of a separate water feed to the lower section of the column.

In addition, regulation of the reflux rate is preferably employed to control the amount of water in the bottoms product.

Regulation of the reflux rate and said separate water feed is preferably effected in dependence upon the concentration of water in the bottoms product, such regulation conveniently being carried out so as to maintain the water concentration within predetermined limits, for instance as specified hereinafter.

In the preferred embodiment of the invention the separate water feed is introduced into the column at a location corresponding to or below the lower limit of the azeotropic zone.

One application of the present invention is especially suitable, but not necessarily limited to, the control of trayed columns where the use of reflux rate regulation to control the bottoms product water concentration tends to have a very slow response rate. The provision of a separate water feed to the base of the column allows a fast responding control loop to be established which, in conjunction with the slow acting control loop established by regulation of the reflux rate, allows the bottoms product water concentration to be maintained within desired limits.

A further advantage secured by the provision of the separate water feed (applicable to both trayed and packed columns) is that sudden reduction or loss of water supplied to the column via the feed stream, eg as a result of a reactor trip in the case where the feed stream is derived from the oxidation process associated with the production of terephthalic acid, can be readily compensated for. For instance, in the event of loss of the feed stream as a result of a reactor trip, the entrainer will rapidly strip out all of the water from the base of the distillation column resulting in loss of the column profile (making it more difficult to re-establish normal operation) and eventually leading to corrosion difficulties in that zone. By monitoring the water concentration in the base of the column (eg by monitoring temperature and/or on-line analysis), a safeguard against such circumstances may be provided by control of the separate water feed to the column.

The liquid phase medium may comprise an aliphatic carboxylic acid, such as acetic acid, and water.

The process of the invention has particular application to azeotropic distillation carried out in such a way as to secure a predetermined amount of water in the bottoms product—for instance, in situations where the bottoms product is required to have a certain water content for compatability with subsequent use of the bottoms product, eg recycle of acetic acid to the oxidation reactor in plant for the production of terephthalic acid.

Where the liquid phase medium comprises an aliphatic carboxylic acid, such as acetic acid, and water, any suitable compound forming a heterogeneous azeotrope with water may be employed, eg alkyl acetates such as n-butyl acetate, iso-butyl acetate and n-propyl acetate.

Although this last-defined aspect of the invention may conveniently be used in processes according to earlier defined aspects of the invention, it is not limited to those processes and may for example be used in processes in which both the organic and aqueous phases are refluxed back to the distillation column.

DETAILED DESCRIPTION OF THE INVENTION

Figure 1:
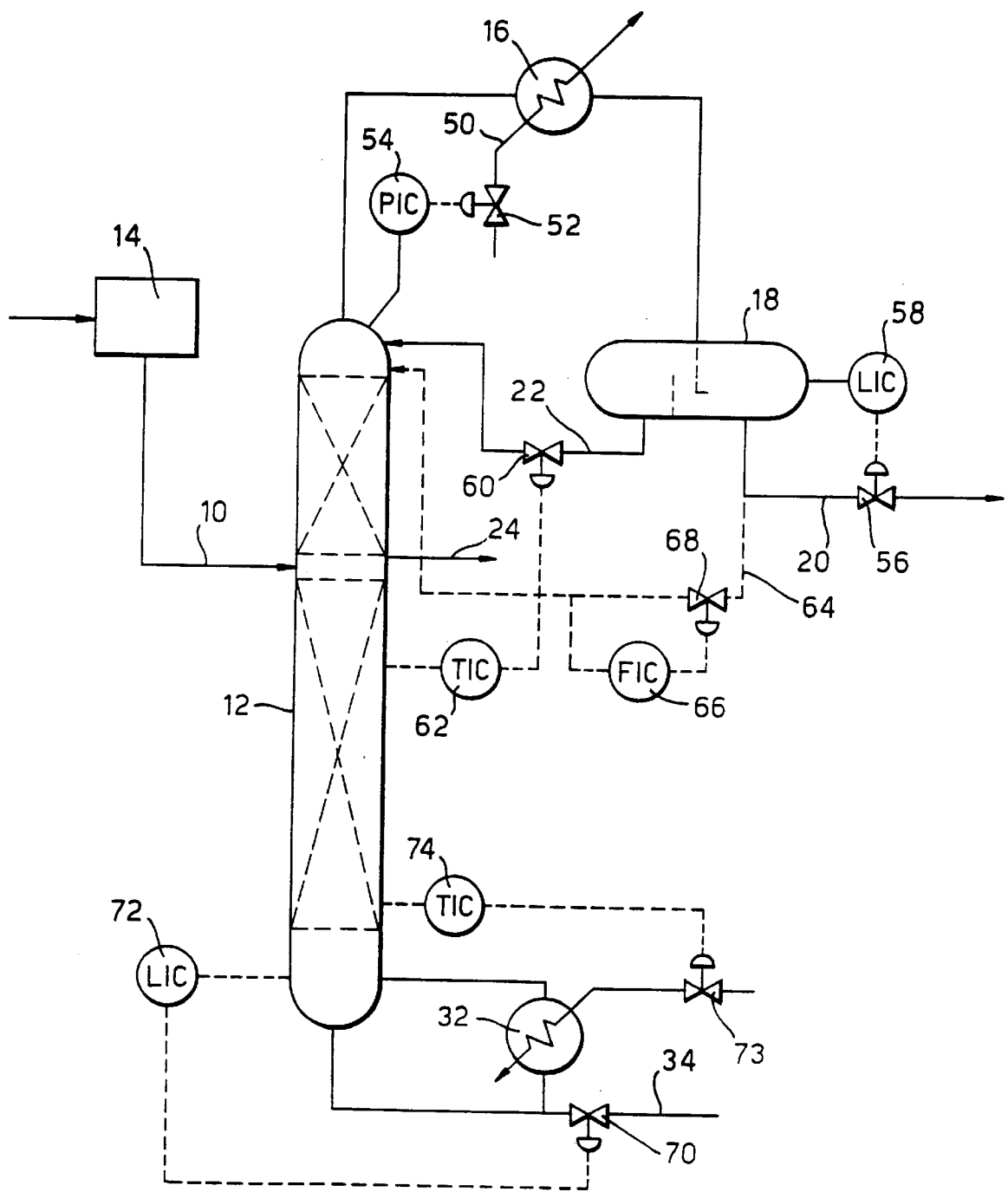
FIG. 1 is a schematic view of an azeotropic distillation plant in accordance with the invention.

The invention will be illustrated by reference to the processing of an aqueous acetic acid stream derived from plant for producing terephthalic acid by the liquid phase oxidation of paraxylene. The oxidation is carried out in a reactor in which the liquid phase medium comprises paraxylene, acetic acid solvent, some water and a brominated catalyst system comprising cobalt and manganese compounds. Such an oxidation process is described in our prior EP-A-498501 and EP-A-502628, the disclosures of which are incorporated herein by this reference. The oxidation process results in the generation of a reactor overhead vapor comprising mainly acetic acid and water of reaction together with other compounds such as methyl acetate and paraxylene. This overhead vapor is withdrawn from the reactor and is partially condensed in an overheads condenser system to produce liquid phase aqueous acetic acid components, a water-lean component which is returned to the reactor as a reflux and a water-rich component which is passed to the distillation column. The latter component contains a water content of the order of 20 to 30% (typically 25 to 28%) by weight based on the combined acetic acid and water content of the stream. The aqueous acetic acid stream usually also contains some paraxylene and methyl acetate.

In the process of the present invention, such recovery is effected using azeotropic distillation in such a way as to produce a bottoms product comprising acetic acid with a reduced water content (typically 5% by weight based on the combined acetic acid/water content) whereby the water content in the oxidation reactor can be regulated by removing excess water and returning a residual amount together with the recycled acetic acid. The lower reflux ratios that can be employed through use of high boiling point entrainers such as n-butyl acetate make such entrainers the logical choice for the azeotropic distillation, especially where the intention is to make more effective use of the significant waste heat generated in the oxidation reaction or to operate the oxidation process at reduced pressure with attendant reduced energy input requirements. However, the water content present in the overheads aqueous acetic acid stream and that present in the acetic acid product derived from the azeotropic distillation are such that high boiling point entrainers require special steps to be taken to prevent slippage of the entrainer into the bottoms product; for instance, operation with a combined organic phase and aqueous phase reflux and/or processing of the reactor overheads stream to increase the water content of the feed to a level effective to strip out substantially all of the entrainer above the point of withdrawal of the bottoms product from the distillation column.

These complications can be avoided by limiting the processing of the overheads aqueous acetic acid stream coupled with operating the distillation process with a single organic phase reflux and so that the acetic add bottoms product is substantially entrainer free and contains the requisite level of water consistent with recycle to the oxidation reactor. This is achieved by using a relatively low boiling point entrainer such as n-propyl acetate, iso-butyl acetate or a compound which has an intermediate boiling point, is compatible with the desired separation and forms a heterogeneous azeotrope with water. By "limiting processing of the reactor overheads aqueous acetic acid stream" we mean that the vapor phase reactor overheads are subjected to condensation processes without taking special additional steps to increase the water content by way of additional rectification equipment.

Referring to the drawing, the feed 10 to the distillation column 12 (which may be a packed column or a trayed column) is obtained directly from the reactor overheads condenser system 14 associated with the oxidation reactor of plant for the production of terephthalic acid, ie without any intervening rectification process, to provide a feed with a high water content in excess of 40%. A low boiling point entrainer such as n-propyl acetate is used and the column is operated so as to secure penetration of the entrainer to a level below the feed 10 whereby the feed 10 enters the column at an entrainer-rich region. Although only one feed is illustrated in the drawing, there may be additional aqueous feeds (liquid phase and/or vapor phase) to the column at other points along the height of the column, eg feeds derived from the high pressure absorber and the first and second crystallisers associated with the oxidation reactor. Such additional feeds may or may not enter the column in the azeotropic zone. The primary feed will be that derived from the overheads condenser system 14 which will generally contribute more water than any other feeds present. In some cases, such other feeds may be combined with the feed from the overheads condenser system 14 and introduced into the column as a single feed.

The tops product at the head of the column 12 is cooled in column overheads condenser system 16 and the condensate is supplied to a phase separator 18 where the condensate is separated into an organic phase (primarily entrainer and a small quantity of water and some methyl acetate, paraxylene and other organics) and an aqueous phase containing a small quantity of entrainer and, inter alia, some methyl acetate.

Although not shown, the phase separator 18 is provided with an outlet for purging of gaseous inerts from the system. To regulate the pressure in the column 12, the cooling medium supplied to cooling system 16 is fed via line 50 under the control of valve 52 controlled by a pressure controller 54. In this way, the pressure within the column 12 can be regulated by adjustment of the flow in line 50. Alternatively the pressure in the column may be regulated by other expedients such as inert blanketing or liquid logging of the condenser 16. The condensed aqueous phase is supplied via line 20 to a stripping column (not shown) where the entrainer is recovered for recycle to the distillation column and methyl acetate is separated as the tops product for subsequent processing. The flow in line 20 is regulated by a valve 56 which is controlled by level controller 58 responsive to the phase interface level within the phase separator 18. In this manner, mass balance at the top of the column is maintained by take off of the aqueous phase under the control of valve 56. The organic phase is returned to the column 12 as a reflux via line 22 regulated by a valve 60 controlled by temperature controller 62 which is responsive to the temperature profile within the distillation column 12. In accordance with certain aspects of the present invention, none of the aqueous phase obtained from the separator 18 is recycled to the column as a reflux. Thus, a single phase reflux is employed thereby securing the advantages previously referred. However, as mentioned previously, we do not exclude the possibility of reflux of the aqueous phase and provision is made in the drawing for this possibility by the inclusion of line 64 with associated flow controller 66 and flow regulating valve 68.

Mass balance is maintained at the base of the column 12 by withdrawing the bottoms product via line 34 at a rate determined by the setting of valve 70 which is regulated by level controller 72. The separation efficiency is maintained by controlling the heat supplied to the reboiler 32 by means of valve 73 which is coupled to temperature controller 74 for sensing the temperature at or near the base of the column.

As mentioned, the column is operated so as to ensure that the entrainer penetrates down the column to a level below the point at which the feed 10 is introduced. Because the entrainer has a low boiling point well removed from that of acetic acid, control of entrainer penetration can be readily achieved without the risk of penetration into the bottoms product withdrawn via line 34. Such control can be implemented by monitoring temperature at a number of vertically spaced locations within the column since the position where the entrainer concentration falls sharply within the column is accompanied by a corresponding sharp change in the temperature profile in that region. By monitoring the temperature profile by means of controller 62, the extent of penetration of the entrainer can be measured and suitable feedback control of the reflux rate via valve 60 and/or reboil rate (via reboiler 32) can be used to adjust entrainer penetration to within predetermined limits. Also, penetration may be controlled by other means such as splitting the reflux into two or more streams, one of which is introduced at the top of the column and the other(s) of which are introduced at one or more lower points—as disclosed in U.S. Pat. No. 2,050,234.

Where a lower boiling point entrainer such as n-propyl acetate is employed (which results in a higher organic reflux ratio than n-butyl acetate for organic phase only reflux), it is feasible to minimise the reflux ratio, more specifically the internal reflux ratio of the column, by varying the amount of sub-cooling that takes place in the condenser system 16. We have found that it is possible to minimise the internal reflux ratio by selection of an appropriate exit temperature from the condenser system 16. Thus, for example, in the case of n-propyl acetate entrainer, we have found that the column internal reflux ratio is at or close to its minimum value if the temperature at the exit of the condenser system 16 is set at about 75° C. Thus, it is preferred that the condenser exit temperature is within about 10° C., more preferably within about 5° C., of the value corresponding to the minimum column internal reflux ratio. By minimising the column internal reflux ratio In this way, both the column diameter and the energy requirements for the distillation can be reduced.

One of the major impurities that tend to be present in the feed 10 derived from the oxidation reactor is paraxylene which has a relatively high boiling point and forms an azeotrope with water. If not removed from the distillation column, the paraxylene present in the feed will tend to accumulate and, as its concentration increases, will tend to impair the performance of the column. We have determined that, if small amounts of paraxylene are present in the feed 10, the concentration profile of paraxylene in the column surprisingly tends to increase markedly in the vicinity of the point of introduction of the feed stream 10. Accordingly, paraxylene removal is effected via line 24 in the vicinity of the point of introduction of the feed stream 10. In this way, the impurity can be removed very effectively without removing excessive amounts of the desired entrainer from the column. In contrast, if n-butyl acetate is used as the entrainer, the paraxylene tends to be more uniformly dispersed throughout the column and cannot be removed in significant quantities at a single location.

In practice, we have found that it is expedient to remove the paraxylene at a location slightly removed from the point at which it reaches its peak concentration relative to the entrainer concentration. Experimental work has established that the ratio of paraxylene concentration to entrainer concentration peaks at a location just below the point of introduction of the aqueous acetic add feed stream 10. However, it has also been established that the relative concentration of toluene, another impurity that tends to be present in the feed stream 10, falls markedly below the point of introduction of the feed stream 10. By purging paraxylene from the column at a location just above the point of introduction of feed stream 10 (ie a location where the ratio of paraxylene to entrainer concentrations is less than its maximum value), a significant amount of toluene can be removed at the same time thereby avoiding the need for separate draw-offs for the paraxylene and toluene impurities.

Figure 2:
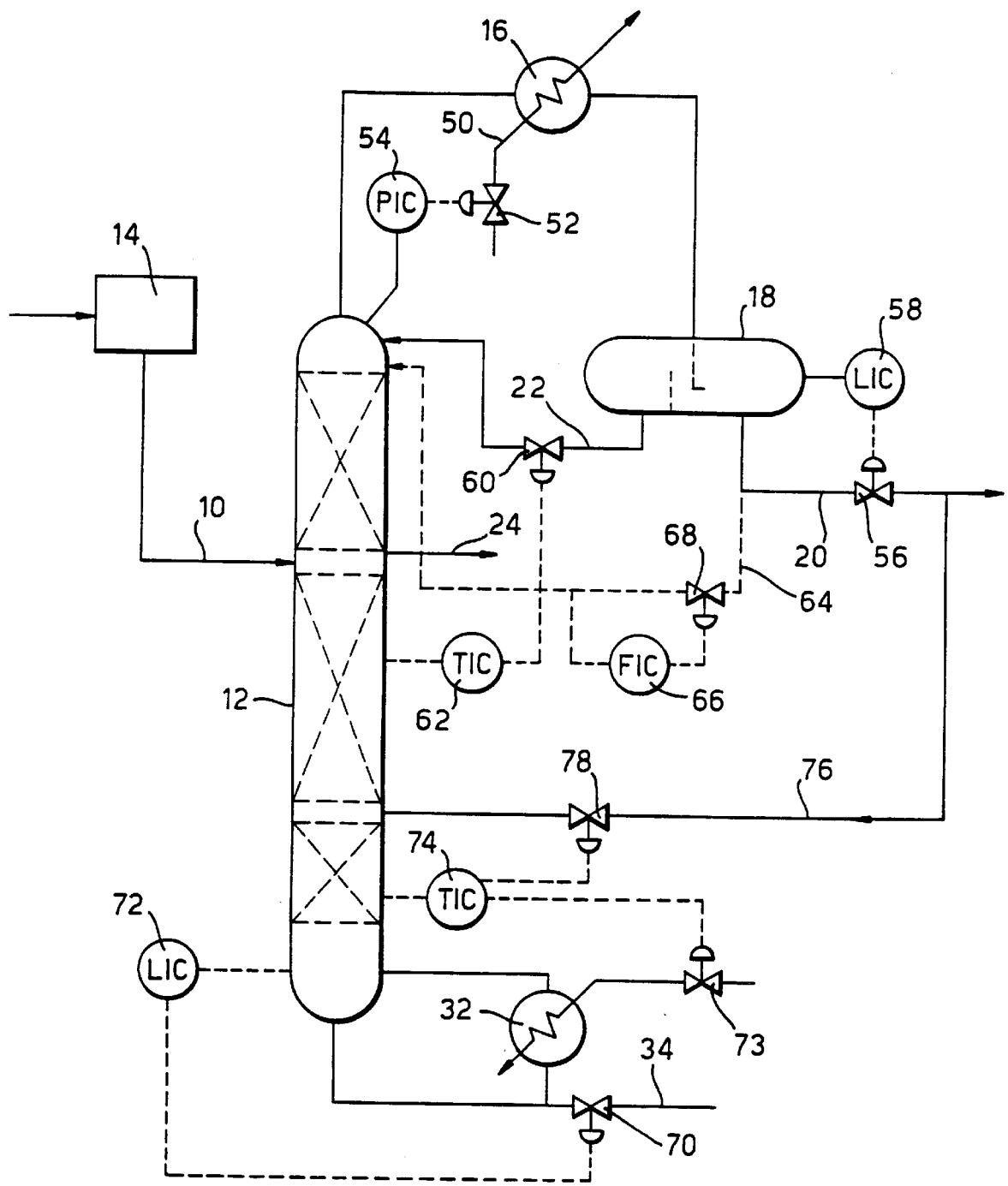
FIG. 2 is a view similar to that of FIG. 1 showing a modified control scheme.

Referring now to FIG. 2, this illustrates a control scheme for accommodating disturbances or loss of feed(s) to the distillation column. The scheme shown in FIG. 2 is similar in many respects to that of FIG. 1 and the same references have been used to depict like components. The key feature in the control scheme of FIG. 2 is the provision for supply of water (via line 76) to the lower section of the column under the control of valve 78 which in turn is controlled by the temperature controller 74. As shown, the water supply is derived from the water exported from the system via line 20. However, the water employed for this purpose may be derived from other sources. Thus, in circumstances where the temperature increases in the base of the column as detected by controller 74 (eg as a result of a substantial or total loss of feed to the column), the setting of the valve 78 is adjusted to admit water into the column of the base to offset the temperature increase and provide water on which the column can work. In a modification of this scheme, the roles of the temperature controllers 62 and 74 may be reversed so that temperature controller 62 controls the valve 73 while temperature controller 74 controls the valve 60 (and also valve 78).

Figure 3:
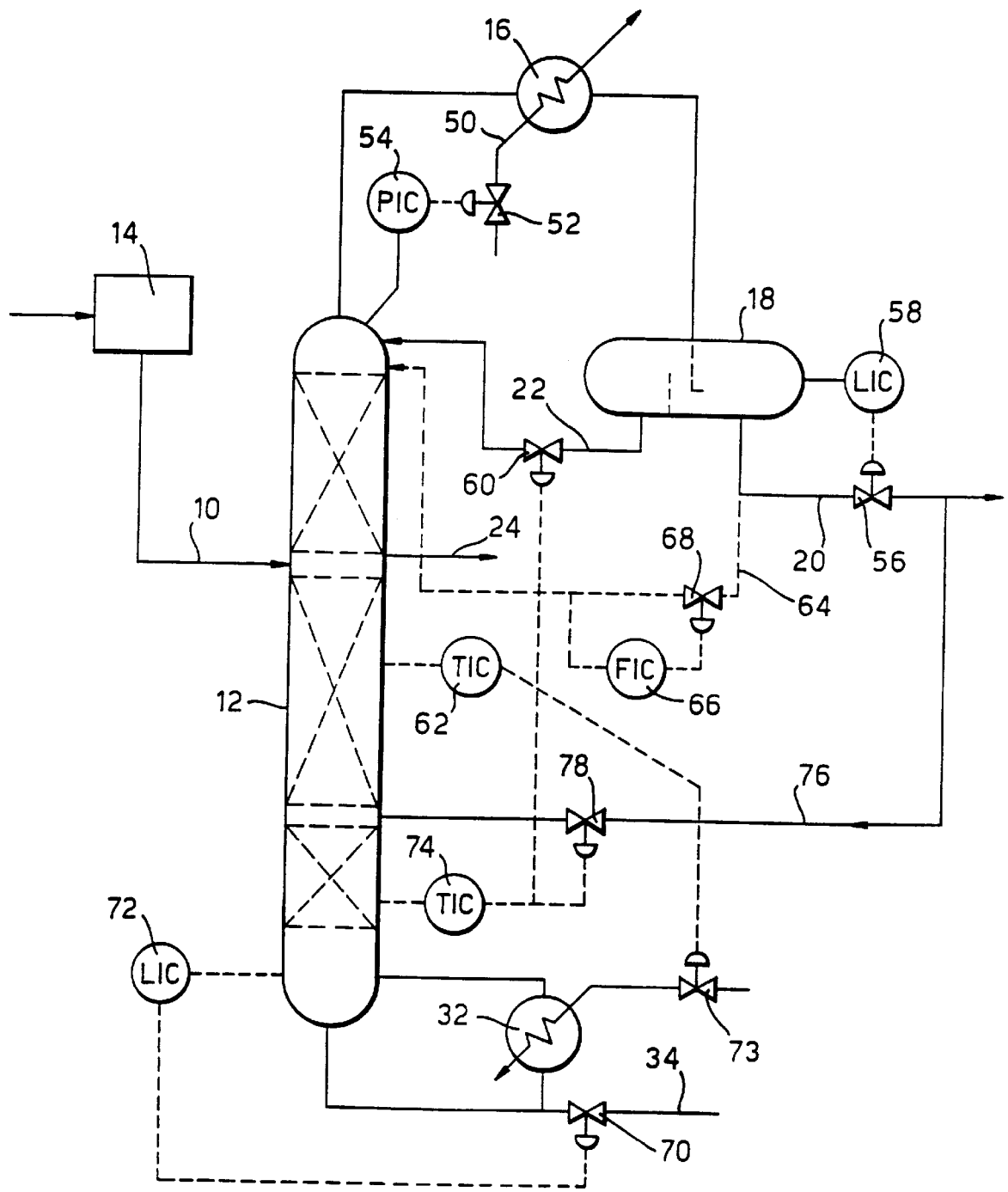
FIG. 3 is a view similar to that of FIG. 2 showing another variant of the control scheme.

A more sophisticated control scheme is shown in FIG. 3. Again the same reference numerals are used to depict similar components in FIGS. 2 and 3. In this scheme, the base temperature controller 74 controls operation of the valves 60 and 78 while controller 62 controls operation of the valve 73. The arrangement is such that, while valve 78 (water supply) can be set by controller 74 to terminate water supply to the column, the valve 60 has a minimum setting which, once attained, is fixed thereby ensuring that there is always at least a predetermined entrainer reflux rate which cannot be reduced further by controller 74. In normal operation of the column, the reflux rate will be fixed to limit the extent of entrainer penetration to an optimum position down the column. In this case, the valve 78 may be set to its closed position so that no water is imported into the column from the line 76.

In a situation where the feed to the column changes, if for instance the temperature in the base of the column 12 is increased in response to entrainer penetration beyond the optimum point, this temperature increase is detected by controller 74 which operates to open valve 78 to admit water thereby giving a fast response to temperature change. At the same time, the increased signal from the controller 74 is detected and the setting of the valve 60 is modified to reduce the reflux rate to the column. This in turn reduces the extent of entrainer penetration down the column with consequent change in the column temperature profile. As the entrainer penetration level rises in the column, the reboiler turns down (under the control of controller 62) with accompanying reduction of temperature in the base of the column and closure (partial or complete) of the valve 78. Thus, the water admission valve provides a fast response loop to variations whilst the reflux valve 60 provides slower response loop which gradually restores column operation to a condition where no or minimal water importation via valve 78 is required.

In extreme circumstances involving substantial or total loss of feed to the column, this will result in an increase in temperature in the base of the column which is counteracted by opening of the water admission valve 78. As described above, the valve 60 is also adjusted to reduce entrainer reflux to the column. However, in these circumstances, closure of the valve 60 is only permitted until the predetermined minimum reflux rate is reached and as the reflux rate reduces, the reboiler 32 in response to the signal generated by controller 62 turns down to an extent determined by the minimum reflux rate. The limit imposed on closure of the valve 60 of course imposes a limit on the extent to which the reboiler can turn down. Thus, in the circumstances, the temperature in the base of the column becomes effective to maintain sufficient water supply to the column via valve 78 in order to provide water on which the column can work and also to prevent slippage of entrainer into the bottoms product.

From the foregoing, it will be seen that the separate small water feed 76 to the lower section of the column with regulation of this water feed in accordance with bottoms product water concentration (eg as measured by temperature changes or on-line analysis) provides fast response to any changes in water concentration thereby maintaining close control over the water content of the bottoms product. Two variables are used to control the bottoms product water concentration, namely the separate water feed and the organic phase reflux rate. The water feed provides fast response whilst the organic phase reflux changes gradually in such a way as to minimise the water feed and restore the concentration within desired limits. Both the water feed and the reflux rate are controlled in dependence upon the bottoms product water concentration (eg as determined by temperature measurements or on-line analysis).

Also as mentioned previously, the separate water feed via line 76 can be used to safeguard against reactor trips which would otherwise result in stripping out of substantially all of the water in the bottom of the column. In this instance, the separate water feed is brought into play in the event of a significant temperature increase in the base region of the column.

It is to be understood that, whilst described in the context of azeotropic distillation using a single organic phase reflux, those schemes involving supply of water to the lower section of the column may also be applied to azeotropic distillation in which both the organic and aqueous phases are refluxed to the column.

We claim:

1. In a process for the production of an aromatic dicarboxylic acid which includes the steps of oxidizing a precursor of the dicarboxylic acid in an aqueous liquid phase medium comprising a lower aliphatic carboxylic acid and in the presence of a heavy metal catalyst system wherein the aromatic dicarboxylic acid is terephthalic acid and the precursor is paraxylene, the oxidation being accompanied by the production of an overhead vapor stream comprising the aliphatic carboxylic acid, water and any amount of precursor which has carried over from the oxidation reaction, condensing the overhead vapor stream to produce a liquid phase feed stream containing the aliphatic carboxylic acid, water and any amount of precursor which may have been present in the overhead vapor stream, and azeotropically distilling the feed stream in an azeotropic distillation column to produce a bottoms product containing the aliphatic carboxylic acid and a reduced amount of water and a tops product having an organic phase and an aqueous phase, the improvement comprising:

(a) operating the azeotropic distillation column with the feed stream having a water content within the range of from 20% to 40% by weight based on the combined weight of the aliphatic carboxylic acid and water in the feed stream and introducing said feed stream into the azeotropic distillation column at a location at, below, or above a lower limit of an azeotropic zone therein and withdrawing and recovering said precursor from the column in a region at, below or above the location of introduction of said feed stream;

(b) using an entrainer selected from the group consisting of isobutyl acetate, n-propyl acetate or an entrainer with a boiling point between the boiling points of isobutyl acetate and n-propyl acetate where the concentration of the entrainer in the combined organic and aqueous liquid phases is at least 0.1% by weight;

(c) separating the tops product into an organic phase comprising the entrainer and an aqueous phase, and recycling the organic phase to the column as a single organic phase reflux; and (d) operating the column whereby the bottoms product is substantially free of said entrainer and contains an amount of water within the range of from 2 to 12% by weight based on the combined weight of the aliphatic carboxylic acid and water in the bottoms product.

2. The process as claimed in claim 1 wherein the improvement comprises the additional step of processing the overhead vapor stream from the oxidation reaction with or without the addition of water from other sources to maintain the concentration of water in the feed stream in the range of from 20 to 40% by weight relative to the combined aliphatic carboxylic acid and water in the feed stream.

3. The process as claimed in claim 1 or 2 in which the azeotropic zone has the lower limit which is located below the point of introduction of said feed stream, and n-propyl acetate is employed as the entrainer.

4. The process as claimed in claim 1 or 2 in which the amount of water in the bottoms product is controlled by regulating a separate water feed to a lower section of the column.

5. The process as claimed in claim 4 in which the separate water feed is introduced into the column at a location corresponding to or below the lower limit of the azeotropic zone.

6. The process as claimed in claim 1 or 2 in which the amount of water in the bottoms product is controlled jointly by regulating a water feed to a lower section of the column and at the same time regulating the rate at which the organic phase is recycled to the column.

7. The process as claimed in claim 1 in which the azeotropic distillation column is a packed column having a packing material selected from random packing or structured packing.

* * * * *